(12) United States Patent
    Ruehle

(10) Patent No.:    US 12,586,661 B2
(45) Date of Patent:        Mar. 24, 2026

(54) HARDWARE ACCELERATED K-MER GRAPH GENERATION

(71) Applicant: Illumina, Inc., San Diego, CA (US)

(72) Inventor: Michael Ruehle, Fort Worth, TX (US)

(73) Assignee: ILLUMINA, INC., San Diego, CA (US)

( * ) Notice: Subject to any disclaimer, the term of this patent is extended or adjusted under 35 U.S.C. 154(b) by 1295 days.

(21) Appl. No.: 17/224,496

(22) Filed: Apr. 7, 2021

(65) Prior Publication Data

US 2021/0313009 A1     Oct. 7, 2021

Related U.S. Application Data

(60) Provisional application No. 63/006,668, filed on Apr. 7, 2020.

(51) Int. Cl.
    *G16B 20/20*        (2019.01)
    *G16B 30/00*        (2019.01)

(52) U.S. Cl.
    CPC ............. *G16B 20/20* (2019.02); *G16B 30/00* (2019.02)

(58) Field of Classification Search
    CPC ........ G16B 20/20; G16B 30/00; G16B 30/20; G16B 50/00; G06F 15/7839
    See application file for complete search history.

(56) References Cited

U.S. PATENT DOCUMENTS

2015/0339437 A1    11/2015    McMillen et al.
2016/0180019 A1    6/2016    Van Rooyen et al.

2016/0259880 A1 *    9/2016    Semenyuk ............. G16B 15/00
2016/0306922 A1    10/2016    Van Rooyen et al.
2016/0306923 A1    10/2016    Van Rooyen et al.
2017/0364666 A1    12/2017    Fisher et al.
2018/0137387 A1    5/2018    Lee et al.
2018/0189444 A1    7/2018    Van Rooyen et al.
            (Continued)

FOREIGN PATENT DOCUMENTS

CN            10246015        3/2015
CN        108334750 A        7/2018
            (Continued)

OTHER PUBLICATIONS

S. M. Bose, V. S. Lalapura, S. Saravanan and M. Purnaprajna, "k-Core: Hardware Accelerator for k-Mer Generation and Counting used in Computational Genomics," 2019 32nd International Conference on VLSI Design and 2019 18th International Conference on Embedded Systems (VLSID), 2019, 347-352 (Year: 2019).*

(Continued)

*Primary Examiner* — Larry D Riggs, II
*Assistant Examiner* — Emilie A Neulen
(74) *Attorney, Agent, or Firm* — Heslin Rothenberg Farley Mesiti P.C.

(57)                ABSTRACT

Methods, systems, and apparatus for hardware-accelerated generation of a K-mer graph using a programmable logic device. In one aspect, a method includes actions of obtaining a first set of nucleic acid sequences, generating a K-mer graph using the obtained first set of nucleic acid sequences and using a plurality of non-pipelined hardware logic units of a programmable logic device, and periodically updating, with a control machine, graph description data for the K-mer graph after performance of the one or more operations by each hardware logic unit.

20 Claims, 5 Drawing Sheets

(56)                References Cited

U.S. PATENT DOCUMENTS

| 2019/0259468 A1 | 8/2019 | Ojard |
| 2019/0306922 A1 | 10/2019 | Van Rooyen et al. |
| 2020/0104464 A1 | 4/2020 | Kaufman et al. |

FOREIGN PATENT DOCUMENTS

| CN | 109416928 A | 3/2019 |
| CN | 109935274 A | 6/2019 |
| CN | 110875084 A | 3/2020 |
| KR | 101188886 B1 | 10/2012 |
| RU | 2586502 | 6/2016 |

OTHER PUBLICATIONS

Laehnemann et al., "Denoising DNA deep sequencing data—high-throughput sequencing errors and their correction," Briefings in Bioinformatics, Jan. 1, 2016, 17(1):154-79.

PCT International Preliminary Report on Patentability in International Appln. No. PCT/US2021/026242, dated Oct. 20, 2022, 9 pages (with English translation).

PCT International Search Report and Written Opinion in International Appln. No. PCT/US2021/026242, dated Jul. 16, 2021, 12 pages.

RU Office Action in Russian Appln. No. 202113518, dated Jun. 14, 2023, 22 pages.

CA Office Action in Canadian Appln. No. 3145326, mailed on Apr. 23, 2024, 5 pages.

CN Office Action in Chinese Appln. No. 2021800040030, mailed on January 4, 202180004003.0 2024, 25 pages (with English translation).

CN Office Action in Chinese Appln. No. 2021800040030.0, mailed on Jul. 13, 2024, 29 pages (with English translation) 202180004003.0.

* cited by examiner

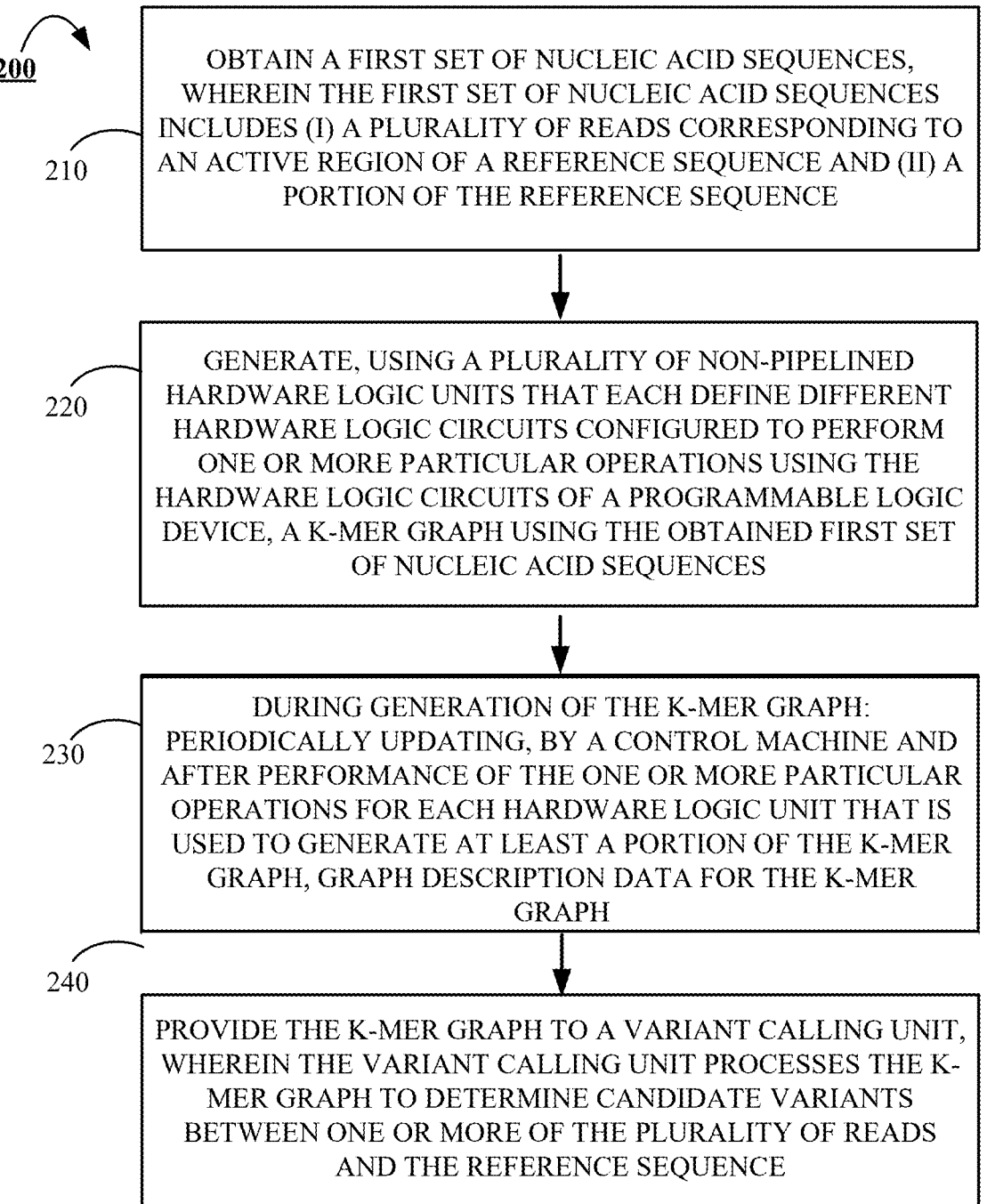

200

210   OBTAIN A FIRST SET OF NUCLEIC ACID SEQUENCES, WHEREIN THE FIRST SET OF NUCLEIC ACID SEQUENCES INCLUDES (I) A PLURALITY OF READS CORRESPONDING TO AN ACTIVE REGION OF A REFERENCE SEQUENCE AND (II) A PORTION OF THE REFERENCE SEQUENCE

220   GENERATE, USING A PLURALITY OF NON-PIPELINED HARDWARE LOGIC UNITS THAT EACH DEFINE DIFFERENT HARDWARE LOGIC CIRCUITS CONFIGURED TO PERFORM ONE OR MORE PARTICULAR OPERATIONS USING THE HARDWARE LOGIC CIRCUITS OF A PROGRAMMABLE LOGIC DEVICE, A K-MER GRAPH USING THE OBTAINED FIRST SET OF NUCLEIC ACID SEQUENCES

230   DURING GENERATION OF THE K-MER GRAPH: PERIODICALLY UPDATING, BY A CONTROL MACHINE AND AFTER PERFORMANCE OF THE ONE OR MORE PARTICULAR OPERATIONS FOR EACH HARDWARE LOGIC UNIT THAT IS USED TO GENERATE AT LEAST A PORTION OF THE K-MER GRAPH, GRAPH DESCRIPTION DATA FOR THE K-MER GRAPH

240   PROVIDE THE K-MER GRAPH TO A VARIANT CALLING UNIT, WHEREIN THE VARIANT CALLING UNIT PROCESSES THE K-MER GRAPH TO DETERMINE CANDIDATE VARIANTS BETWEEN ONE OR MORE OF THE PLURALITY OF READS AND THE REFERENCE SEQUENCE

FIG. 2

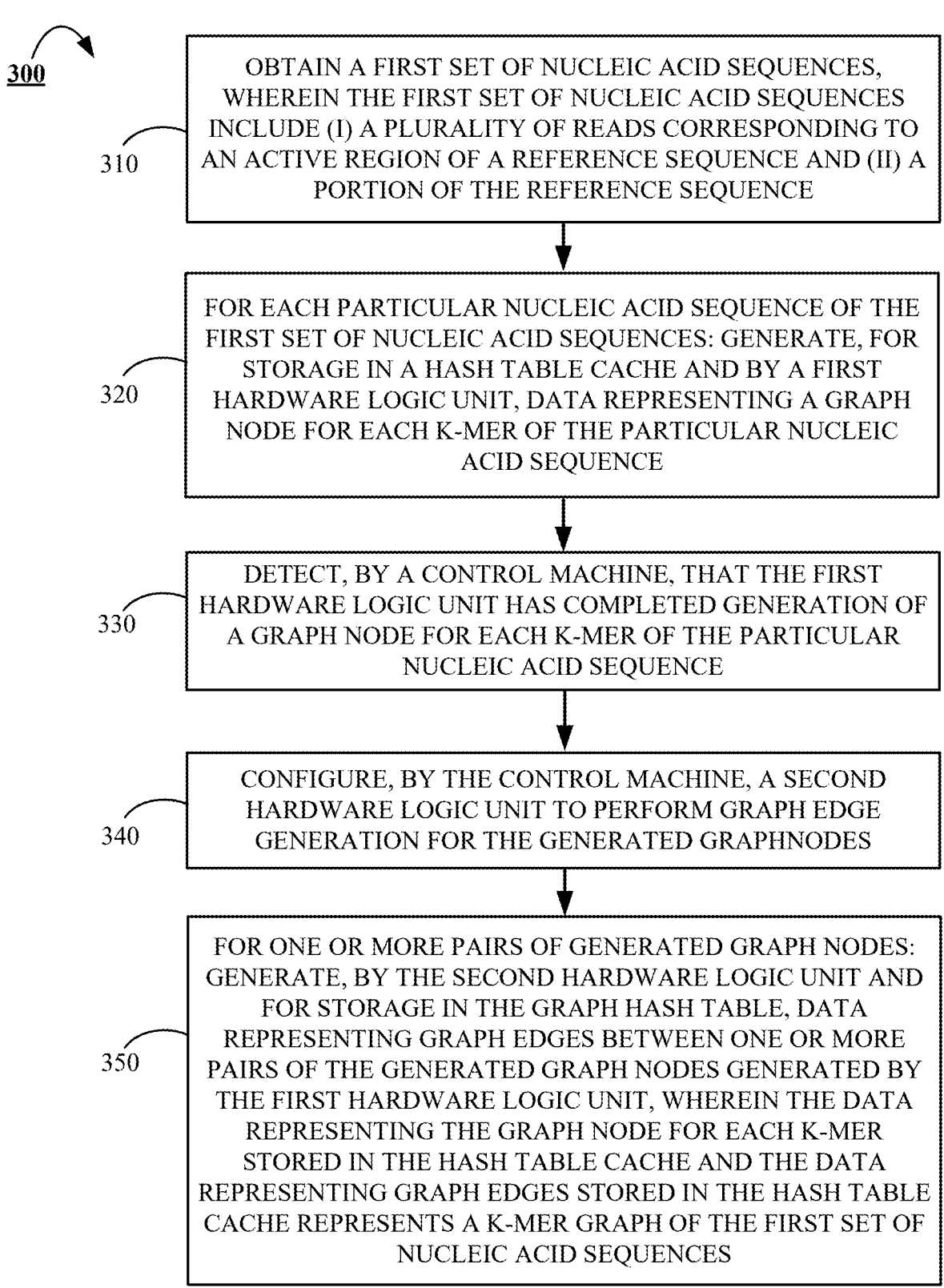

300

310 OBTAIN A FIRST SET OF NUCLEIC ACID SEQUENCES, WHEREIN THE FIRST SET OF NUCLEIC ACID SEQUENCES INCLUDE (I) A PLURALITY OF READS CORRESPONDING TO AN ACTIVE REGION OF A REFERENCE SEQUENCE AND (II) A PORTION OF THE REFERENCE SEQUENCE

320 FOR EACH PARTICULAR NUCLEIC ACID SEQUENCE OF THE FIRST SET OF NUCLEIC ACID SEQUENCES: GENERATE, FOR STORAGE IN A HASH TABLE CACHE AND BY A FIRST HARDWARE LOGIC UNIT, DATA REPRESENTING A GRAPH NODE FOR EACH K-MER OF THE PARTICULAR NUCLEIC ACID SEQUENCE

330 DETECT, BY A CONTROL MACHINE, THAT THE FIRST HARDWARE LOGIC UNIT HAS COMPLETED GENERATION OF A GRAPH NODE FOR EACH K-MER OF THE PARTICULAR NUCLEIC ACID SEQUENCE

340 CONFIGURE, BY THE CONTROL MACHINE, A SECOND HARDWARE LOGIC UNIT TO PERFORM GRAPH EDGE GENERATION FOR THE GENERATED GRAPHNODES

350 FOR ONE OR MORE PAIRS OF GENERATED GRAPH NODES: GENERATE, BY THE SECOND HARDWARE LOGIC UNIT AND FOR STORAGE IN THE GRAPH HASH TABLE, DATA REPRESENTING GRAPH EDGES BETWEEN ONE OR MORE PAIRS OF THE GENERATED GRAPH NODES GENERATED BY THE FIRST HARDWARE LOGIC UNIT, WHEREIN THE DATA REPRESENTING THE GRAPH NODE FOR EACH K-MER STORED IN THE HASH TABLE CACHE AND THE DATA REPRESENTING GRAPH EDGES STORED IN THE HASH TABLE CACHE REPRESENTS A K-MER GRAPH OF THE FIRST SET OF NUCLEIC ACID SEQUENCES

FIG. 3

HARDWARE ACCELERATED K-MER GRAPH GENERATION

CROSS-REFERENCE TO RELATED APPLICATIONS

This application claims the benefit of U.S. Provisional Patent Application No. 63/006,668 filed Apr. 7, 2020, the entire contents of which is incorporated herein by reference in its entirety.

BACKGROUND

K-mer graphs can be used to represent a plurality of sequencing reads.

SUMMARY

According to one innovative aspect of the present disclosure, a method for hardware-accelerated generation of a K-mer graph using a programmable logic device is disclosed. In one aspect, the method can include actions of obtaining a first set of nucleic acid sequences, wherein the first set of nucleic acid sequences includes (i) a plurality of reads corresponding to an active region of a reference sequence and (ii) a portion of the reference sequence, generating, using a plurality of non-pipelined hardware logic units of a programmable logic device, a K-mer graph using the obtained first set of nucleic acid sequences, wherein each hardware logic unit comprises a different hardware logic circuit configured to perform one or more operations, wherein each node of the K-mer graph represents a K-mer, each edge of the K-mer graph represents a link between a pair of K-mers, and each weight of each edge of the K-mer graph represents a number of occurrences of a K-mer sequence represented by a pair of K-mers, and during generation of the K-mer graph: periodically updating, with a control machine, graph description data for the K-mer graph after performance of the one or more operations by each hardware logic unit that is used to generate at least a portion of the K-mer graph, wherein the graph description data represents (i) a K-mer graph identifier and (ii) K-mer graph state information, wherein the control machine creates a workflow of operations using the non-pipelined hardware logic units by triggering performance of the one or more operations of each respective hardware logic unit during generation of the K-mer graph.

Other versions include corresponding systems and apparatus that have been configured to perform the actions of the aforementioned methods defined by hardware logic circuits of a hardware-accelerated graph generation unit.

These and other versions may optionally include one or more of the following features. For instance, in some implementations, the output of each hardware logic unit of the plurality of hardware logic units is stored via a hash table cache.

In some implementations, the control machine is implemented using a hardware logic unit of the programmable logic device.

In some implementations, the control machine is implemented by using one or more CPUs or GPUs to execute software instructions to realize functionality of the control machine.

In some implementations, operations can further include providing the generated K-mer graph to a variant calling unit, wherein the variant calling unit processes the K-mer graph to determine candidate variants between one or more of the plurality of reads and the reference sequence.

In some implementations, software instructions can be executed by one or more CPUs or GPUs to realize one or more functions of the variant calling unit.

In some implementations, programmable logic device is used to accelerate one or more functions of the variant calling unit.

In some implementations, the graph description data further includes (iii) data representing a last hardware logic unit of the plurality of hardware logic units that executed hardware logic on the K-mer graph or nucleic acid sequences of the pileup associated with the K-mer graph identifier.

According to another innovative aspect of the present disclosure, a system for hardware-accelerated generation of a K-mer graph using a programmable logic device is disclosed. In one aspect, the system can include a hardware-accelerated graph generation unit that includes hardware digital logic circuits that have been arranged to perform operations. In some implementations, the operation can comprise: obtaining a first set of nucleic acid sequences, wherein the first set of nucleic acid sequences includes (i) a plurality of reads corresponding to an active region of a reference sequence and (ii) a portion of the reference sequence, generating, using a plurality of non-pipelined hardware logic units of a programmable logic device a K-mer graph using the obtained first set of nucleic acid sequences, wherein each hardware logic unit comprises a different hardware logic circuit configured to perform one or more operations, wherein each node of the K-mer graph represents a K-mer, each edge of the K-mer graph represents a link between a pair of K-mers, and each weight of each edge of the K-mer graph represents a number of occurrences of a K-mer sequence represented by a pair of K-mers, and during generation of the K-mer graph: periodically updating, with a control machine, graph description data for the K-mer graph after performance of the one or more operations by each hardware logic unit that is used to generate at least a portion of the K-mer graph, wherein the graph description data represents (i) a K-mer graph identifier and (ii) K-mer graph state information, wherein the control machine creates a workflow of operations using the non-pipelined hardware logic units by triggering performance of the one or more operations of each respective hardware logic unit during generation of the K-mer graph.

Other versions include corresponding methods and apparatus for performing aforementioned operations.

These and other versions may optionally include one or more of the following features. For instance, in some implementations, the output of each hardware logic unit of the plurality of hardware logic units is stored via a hash table cache.

In some implementations, the system can further include one or more computers, and one or more memory devices storing instructions that, when executed by the one or more computers, cause the one or more computers to perform second operations of a variant calling unit. In some implementations, the second operations of the variant calling unit can include obtaining, by the variant calling unit, the generated K-mer graph, and identifying, based on the variant calling unit processing the generated K-mer graph, one or more candidate variants, wherein a candidate variant is a difference between a base call of one or more reads in the pileup of reads and a nucleotide of a reference genome at a particular location of the reference genome.

In some implementations, operations can further include obtaining, by a variant calling unit, the generated K-mer graph, and identifying, based on the variant calling unit processing the generated K-mer graph, one or more candidate variants, wherein a candidate variant is a difference between a base call of one or more reads in the pileup of reads and a nucleotide of a reference genome at a particular location of the reference genome.

In some implementations, the graph description data can further include (iii) data representing a last hardware logic unit of the plurality of hardware logic units that executed hardware logic on the K-mer graph or nucleic acid sequences of the pileup associated with the K-mer graph identifier.

According to another innovative aspect of the present disclosure, a hardware-accelerated graph generation unit is disclosed. In one aspect, the hardware-accelerated graph generation unit can include hardware digital logic circuits that have been arranged to perform operations. In some implementations, the operations can include obtaining a first set of nucleic acid sequences, wherein the first set of nucleic acid sequences includes (i) a plurality of reads corresponding to an active region of a reference sequence and (ii) a portion of the reference sequence, generating, using a plurality of non-pipelined hardware logic units of a programmable logic device a K-mer graph using the obtained first set of nucleic acid sequences, wherein each hardware logic unit comprises a different hardware logic circuit configured to perform one or more operations, wherein each node of the K-mer graph represents a K-mer, each edge of the K-mer graph represents a link between a pair of K-mers, and each weight of each edge of the K-mer graph represents a number of occurrences of a K-mer sequence represented by a pair of K-mers, and during generation of the K-mer graph: periodically updating, with a control machine, graph description data for the K-mer graph after performance of the one or more operations by each hardware logic unit that is used to generate at least a portion of the K-mer graph, wherein the graph description data represents (i) a K-mer graph identifier and (ii) K-mer graph state information, wherein the control machine creates a workflow of operations using the non-pipelined hardware logic units by triggering performance of the one or more operations of each respective hardware logic unit during generation of the K-mer graph.

According to another innovative aspect of the present disclosure, a method for hardware-accelerated generation of a K-mer graph in a programmable logic device is disclosed. In one aspect, the method can include actions of obtaining a first set of nucleic acid sequences, wherein the first set of nucleic acid sequences include (i) a plurality of reads corresponding to an active region of a reference sequence and (ii) a portion of the reference sequence, for each particular nucleic acid sequence of the first set of nucleic acid sequences: generating, for storage in a hash table cache and by a first hardware logic unit, data representing a graph node for each K-mer of the particular nucleic acid sequence, detecting, by a control machine, that the first hardware logic unit has completed generation of a graph node for each K-mer of the particular nucleic acid sequence, configuring, by the control machine, a second hardware logic unit to perform graph edge generation for the generated graph nodes, and for one or more pairs of the generated graph nodes: generating, by the second hardware logic unit and for storage in the graph hash table, data representing graph edges between one or more pairs of the generated graph nodes generated by the first hardware logic unit, wherein the data representing the graph node for each K-mer stored in the hash table cache and the data representing graph edges stored in the hash table cache represents a K-mer graph of the first set of nucleic acid sequences.

Other versions include corresponding systems and apparatus that have been configured to perform the actions of the aforementioned methods defined by hardware logic circuits of a hardware-accelerated graph generation unit.

These and other versions may optionally include one or more of the following features. For instance, in some implementations, the method can further include evaluating the K-mer graph to check for the existence of graph cycles. In such implementations, if a graph cycle is detected during the evaluation: then the process can include terminating generation of the K-mer graph. Alternatively, if a graph cycle is not detected during the evaluation: the method can include obtaining data from the hash table cache describing the structure of the K-mer graph, and providing, to a variant calling module, the obtained data that describes the structure of the K-mer graph.

In some implementations, method further can further include periodically storing, by the control machine and in a memory unit that is accessible by the control machine, graph description data for an instance of the K-mer graph, wherein the graph description data represents (i) a K-mer graph identifier and (ii) K-mer graph state information.

In some implementations, the first hardware logic unit can be further configured to: determine whether one or more of the particular K-mers of the particular nucleic acid sequence matches another K-mer of the particular nucleic acid sequence, and based on a determination that the one or more particular K-mers of the particular nucleic acid sequence match another K-mer of the particular nucleic acid sequence, store data that marks the one or more particular K-mers as non-unique K-mers.

In some implementations, the second hardware logic is further configured to: assign an edge weight to each edge of the K-mer graph.

In some implementations, the method can further include instructing a third hardware logic unit of the programmable logic device to execute hardware logic configured to: obtain data representing the K-mer graph from the hash table cache, and provide the obtained data representing the K-mer graph to a variant calling unit.

In some implementations, the method can further include instructing a third hardware logic unit of the programmable logic device to execute hardware logic configured to: selectively delete data representing graph nodes and data representing graph edges of the K-mer graph from the hash table cache.

In some implementations, the control machine is implemented using a third hardware logic unit of the programmable logic device.

In some implementations, the hash table cache is implemented using a third hardware logic unit of the programmable logic device.

In some implementations, the control machine is implemented by using one or more CPUs or GPUs that execute software instructions to realize the functionality of the control machine.

In some implementations, the graph description data further includes (iii) data representing a last hardware logic unit of the plurality of hardware logic units that executed hardware logic on the K-mer graph or nucleic acid sequences of the pileup associated with the K-mer graph identifier.

According to another innovative aspect of the present disclosure, a system for hardware-accelerated generation of a K-mer graph using a programmable logic device is disclosed. The system can include a hardware-accelerated graph generation unit that includes hardware digital logic circuits that have been arranged to perform operations. In one aspect, the operations can include obtaining a first set of nucleic acid sequences, wherein the first set of nucleic acid sequences include (i) a plurality of reads corresponding to an active region of a reference sequence and (ii) a portion of the reference sequence, for each particular nucleic acid sequence of the first set of nucleic acid sequences: generating, for storage in a hash table cache and by a first hardware logic unit, data representing a graph node for each K-mer of the particular nucleic acid sequence, detecting, by a control machine, that the first hardware logic unit has completed generation of a graph node for each K-mer of the particular nucleic acid sequence, configuring, by the control machine, a second hardware logic unit to perform graph edge generation for the generated graph nodes, and for one or more pairs of the generated graph nodes: generating, by the second hardware logic unit and for storage in the graph hash table, data representing graph edges between one or more pairs of the generated graph nodes generated by the first hardware logic unit, wherein the data representing the graph node for each K-mer stored in the hash table cache and the data representing graph edges stored in the hash table cache represents a K-mer graph of the first set of nucleic acid sequences.

Other versions include corresponding methods and apparatus for performing aforementioned operations.

These and other versions may optionally include one or more of the following features. For instance, in some implementations, the operations can further include periodically storing, by the control machine and in a memory unit that is accessible by the control machine, graph description data for an instance of the K-mer graph, wherein the graph description data represents (i) a K-mer graph identifier and (ii) K-mer graph state information.

In some implementations, the first hardware logic unit is further configured to: determine whether one or more of the particular K-mers of the particular nucleic acid sequence matches another K-mer of the particular nucleic acid sequence, and based on a determination that the one or more particular K-mers of the particular nucleic acid sequence match another K-mer of the particular nucleic acid sequence, store data that marks the one or more particular K-mers as non-unique K-mers. In such implementations, the second hardware logic is further configured to: assign an edge weight to each edge of the K-mer graph.

According to another innovative aspect of the present disclosure, a hardware-accelerated graph generation unit is disclosed. The hardware-accelerated graph generation unit can include hardware digital logic circuits that have been arranged to perform operations. In one aspect, the operations can include obtaining a first set of nucleic acid sequences, wherein the first set of nucleic acid sequences include (i) a plurality of reads corresponding to an active region of a reference sequence and (ii) a portion of the reference sequence, for each particular nucleic acid sequence of the first set of nucleic acid sequences: generating, for storage in a hash table cache and by a first hardware logic unit, data representing a graph node for each K-mer of the particular nucleic acid sequence, detecting, by a control machine, that the first hardware logic unit has completed generation of a graph node for each K-mer of the particular nucleic acid sequence, configuring, by the control machine, a second hardware logic unit to perform graph edge generation for the generated graph nodes, and for one or more pairs of the generated graph nodes: generating, by the second hardware logic unit and for storage in the graph hash table, data representing graph edges between one or more pairs of the generated graph nodes generated by the first hardware logic unit, wherein the data representing the graph node for each K-mer stored in the hash table cache and the data representing graph edges stored in the hash table cache represents a K-mer graph of the first set of nucleic acid sequences.

These and other aspects of the present disclosure are discussed in more detail in the detailed description below with reference to the accompanying drawings.

BRIEF DESCRIPTION OF THE DRAWINGS

FIG. 2 is a flowchart of an example of a process for hardware-accelerated generation of a K-mer graph.

FIG. 3 is a flowchart of another example of a process for hardware-accelerated generation of a K-mer graph.

DETAILED DESCRIPTION

The present disclosure is directed towards hardware-accelerated generation of a K-mer graph. Generation of the K-mer graph using hardware circuits significantly reduces the amount of time required to generate the K-mer graph and offloads the computationally intensive K-mer graph generation process from a software processor to hardware logic of an integrated circuit such as a field programmable gate array or ASIC. This frees up software resources of the software processor that can be used to perform other genomic data processing tasks.

Hardware-accelerated generation of K-mer graphs can be achieved using a control machine that is configured to manage a workflow of operations performed by a plurality of non-pipelined hardware logic units. In particular, the control machine can abstractly achieve high-level pipelined functionality using the plurality of non-pipelined hardware logic units. The control machine can achieve this functionality by storing and updating graph description data that includes (i) a K-mer graph identifier that identifies an instance of a K-mer graph and (ii) K-mer graph state information. The K-mer graph state information can include, for example, data indicating a last hardware logic unit that operated on raw graph data for a particular instance of a K-mer graph, data indicating whether the last hardware logic unit aborted the operation, data indicating a K-mer length, data indicating a K-mer node list, data indicating a list of pointers that can be used to identify the K-mer nodes in a cache, a length of a K-mer node list, data indicating a list of non-unique K-mers, or any subset or combination thereof. The control machine manages K-mer graph generation by calling a particular hardware logic unit that is to perform an operation on a raw graph data and providing an updated set of graph description data to the called hardware logic unit.

This storage and updating of the graph description data enables the control machine to manage parallel processing of the non-pipelined hardware logic units in a manner that enables each of the non-pipelined hardware logic units to operate on data corresponding to a different K-mer graph. Accordingly, in addition to increased speed benefits achieved using hardware logic instead of execution of software instructions to generate K-mer graphs, the present disclosure achieves further accelerated operation by increasing throughput by generating segments of different K-mer graphs at the same time using different hardware logic units managed by the control machine.

Figure 1:
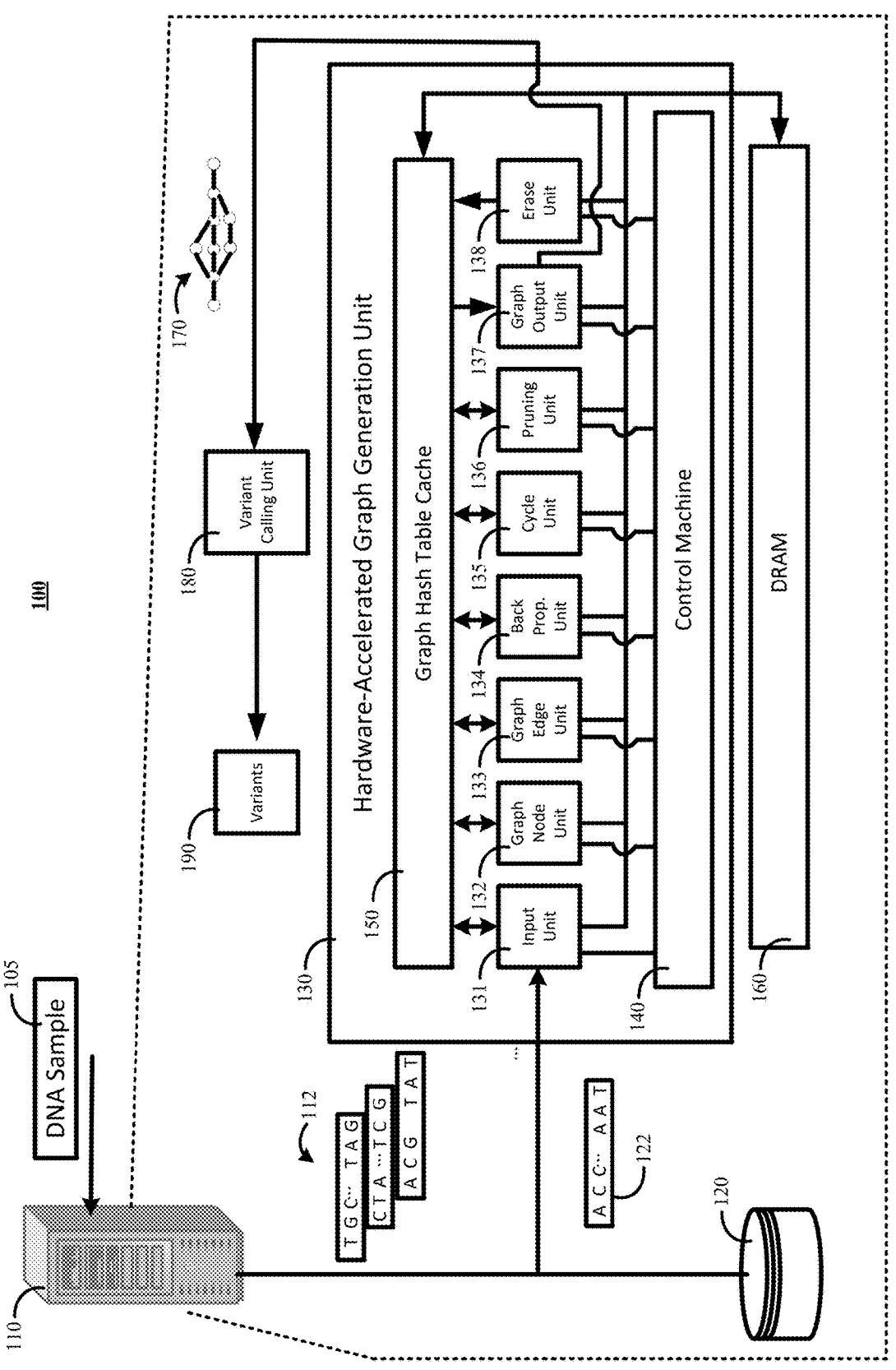
FIG. 1 is an example of a system for hardware-accelerated generation of a K-mer graph.

FIG. 1 is an example of a system 100 for hardware-accelerated generation of a K-mer graph. In some implementations, the system 100 can include a nucleic acid sequencer 110, a reference sequence database 120, a hardware-accelerated graph generation unit 130, a plurality of hardware logic units 131, 132, 133, 134, 135, 136, 137, 138, a control machine 140, a graph hash table cache 150, a DRAM 160, and a variant calling unit 180. In some implementations, the hardware-accelerated graph generation unit 130 can be implemented using a programmable logic circuit such as a field programmable gate array (FPGA). In other implementations, the hardware-accelerated graph generation unit 130 can be implemented using an Application Specification Integrated Circuit (ASIC). In either scenario, the functionality described with respect to the hardware-accelerated graph generation unit 130, and each of the components implemented thereon, is implemented using hardware logic circuits arranged to realize the functionality described herein without executing software instructions to realize the functionality.

The term "unit" is used in this specification to describe a software module, a hardware module, or a combination of both, that is used to perform a specified function. A determination of whether a particular "unit" described herein is hardware, software, or a combination of both, can be made based on the context of its use. For example, an "input unit" 131, a "graph node unit" 132, a "graph edge unit" 133, or the like, resident in a hardware-accelerated graph generation unit 130 that is implemented using an FPGA or ASIC is a hardware unit whose functionality is realized by hardwired digital logic gates or hardwired digital logic blocks that have been arranged to realize the functionality described herein with respect to the particular "unit." By way of another example, a "variant calling unit" 180 that is not implemented using a hardware-accelerated graph generation unit 130 in FIG. 1 is a software module whose functionality is realized by one or more computers executing software instructions defining the functionality of the "variant calling unit" 180. By way of another example, a computer or processing unit can be a hardware device that realizes functionality by processing software instructions, and thus functionality of the computer or processing unit is a combination of hardware and software.

Though examples of one or more components of FIG. 1 are provided herein as hardware implementations such as the "control machine" 140 because the "control machine" is depicted in FIG. 1 as being implemented in the hardware-accelerated graph generation unit 130, the present disclosure is not limited to such examples. Instead, other implementations can be employed where the "control machine" 140 is implemented in software as a software module or a combination of hardware and software with a computer or processing unit executing software instructions to realize the functionality of the "control machine" 140 described here. Likewise, there can be implementations of the present disclosure where certain components described as software with respect to FIG. 1 such as the "variant calling unit" 180 are implemented as a hardware implementation.

The nucleic acid sequencer 110 is a device that is configured to perform primary analysis. Primary analysis can include receiving, by the nucleic acid sequencer 110, a biological sample 105 such as a blood sample, tissue sample, sputum, or nucleic acid and generating, by the nucleic acid sequencer 110, output data such as one or more reads 112 that each represent an order of nucleotides of a nucleic acid sequence of the received biological sample. In some implementations, sequencing, by the nucleic acid sequencer 110, can be performed in multiple read cycles, with a first read cycle generating one or more first reads that include a string of base calls representing an order of nucleotides from a first end of a nucleic acid sequence fragment and a second read cycle generating one or more respective second reads that include a string of base calls representing an order of nucleotides from the other ends of one of the nucleic acid sequence fragments. In some implementations, the reads can be generated using clonal amplification. In the example of FIG. 1, the one or more reads 112 can include a pileup of reads for a particular reference genome location, with the reference genome location being comprised of multiple, sequential reference genome locations.

Thus, each read is data that represents a portion of a nucleic acid genome for an organism such as an animal, insect, plant, or the like. Assuming short nucleic acid sequence fragments of approximately 600 base calls, a first read may represent 150 ordered nucleotides for the first end of the nucleic acid sequence fragment and a second read may represent 150 ordered nucleotides of the other end of the nucleic acid sequence fragment. These numbers, however, are merely examples and any nucleic acid sequencer 110 can be configured to generate reads that can be operated on by a hardware-accelerated graph generation unit as described herein using any sequencing methods. Such reads can be of different lengths than those mentioned here. For example, in some implementations, the present disclosure can be used to generate hardware-accelerated K-mer graphs for reads generated by nucleic acid sequence fragments having up to 1000 nucleotides, or more, with each read having, for example, 50 base calls, 75 base calls, 150 base calls, 200 base calls, 300 base calls, 500 base calls, or more from the end of each fragment. Each base call can correspond to a nucleotide. The present disclosure can also be used to generate hardware-accelerated K-mer graphs for long reads. Accordingly, the hardware-accelerated graph generation unit 130 can be used to generate K-mer graphs for any reads generated in any way by any type of nucleic acid sequencer.

In some implementations, the biological sample 105 can include a DNA sample and the nucleic acid sequencer 110 can include a DNA sequencer. In such implementations, the order of sequenced nucleotides in a read generated by the nucleic acid sequencer can include one or more of guanine (G), cytosine (C), adenine (A), and thymine (T) in any combination. In some implementations, the nucleic acid sequencer 110 can be used to sequence RNA samples. In some implementations, this can occur using RNA-seq protocols. By way of example, an RNA sample can be preprocessed using reverse-transcription to form complementary DNA (cDNA) using a reverse transcriptase enzyme. In other implementations, the nucleic acid sequencer 110 can include an RNA sequencer, and the biological sample can include an RNA sample. Accordingly, though the example of FIG. 1 describes a nucleic acid sequencer that produces reads comprised of Gs, Cs, As, and Ts that is generated by a DNA sequencer based on a DNA sample, the present disclosure is not so limited. Instead, other implementations can process reads comprised of Cs, Gs, As, and Us that are generated by an RNA sequencer based on an RNA sample. In some implementations, the DNA reads or RNA reads generated by the nucleic acid sequencer can include a base call N, with N being indicative of an unknown base call being generated by the nucleic acid sequencer.

In some implementations, the nucleic acid sequencer 110 can include a next generation sequencer (NGS) that is configured to generate sequence reads such as reads 112 for a given sample in a manner that achieves ultra-high throughput, scalability, and speed through the use of massively parallel sequencing technology. The NGS enables rapid sequencing of whole genomes, the ability to zoom into deeply sequenced target regions, utilize RNA sequencing (RNA-Seq) to discover novel RNA variants and splice sites, or quantify mRNAs for gene expression analysis, analysis of epigenetic factors such as genome-wide DNA methylation and DNA-protein interactions, sequencing of cancer samples to study rare somatic variants and tumor subclones, and studying of microbial diversity in humans or in the environment.

The nucleic acid sequencer 110 can obtain a reference genome 122 from the reference genome database 122. In some implementations, only a portion of the reference genome 122 is obtained. The portion of the reference genome 122 that is obtained can correspond to the reference locations of the reference genome 122 that the pileup of reads 112 are mapped and aligned thereto. The reference genome database 122 can include data storage that organizes storage for a plurality of different reference genomes. In some implementations, the particular reference genome 122 selected from the reference genome database can be based on the type of DNA sample 105. In some implementations, the type of reference genome selected 122 selected form the reference genome database 120 can be selected based on input from a user of the nucleic acid sequencer 110. In such implementations, the user can, for example, select a reference genome 120 identifier that can be used, by the nucleic acid sequencer 110, to select a particular reference genome 122 from the reference genome database 120. The reference genome 122 can include, for example, a nucleic acid sequence assembled as a representative example of a set of genes for a particular species.

The combination of the pileup of reads 112 generated by the nucleic acid sequencer 110 and the obtained reference genome 122 can be provided as inputs to the hardware-accelerated graph generation unit 130. These inputs can be processed by one or more of the hardware logic units 131 to 138 of the hardware-accelerated graph generation unit 130 to generate an instance of a K-mer graph. For example, each hardware logic unit of the hardware logic units 131 to 138 can be configured to perform their respective operations for each read of the pileup of reads 112 included as an input to the hardware-accelerated graph generation unit 130.

The system 100 of FIG. 1 is described herein as including a nucleic acid sequencer. In some implementations, such as that described with reference to FIG. 1, the system can include a sequencer 110 and the hardware-accelerated graph generation unit 130, and other components of system 100, can be integrated within the nucleic acid sequencer 110. However, the present disclosure is not limited to being integrated within the nucleic acid sequencer 110. Instead, in some implementations, the hardware-accelerated graph generation unit 130 can be implemented in a programmable logic device or ASIC integrated or housed within a computer that is remote from the nucleic acid sequencer 110 and communicably coupled to the nucleic acid sequencer 110 such as by using one or more wired or wireless networks. Similarly, the database 120, variant calling unit 180, or both, may be implemented outside the nucleic acid sequencer.

110. Likewise, there is no requirement that the system 100 include a nucleic acid sequencer 110 at all. Instead, in some implementations, the hardware-accelerated graph generation unit 130, and other components of FIG. 1, can be implemented in a computer system that does not include a nucleic acid sequencer 110. In such implementations, the hardware-accelerated graph generation unit can obtain the pileup of reads 112, the reference sequence 122, or both, via a network, from a storage location(s) of one or more memory devices, or like. Accordingly, the system 100 depicts an example of the present disclosure but does not limit the present disclosure to any one particular configuration of system components.

The one or more hardware logic units of the hardware-accelerated graph generation unit 130 can include an input unit 131, a graph node unit 132, a graph edge unit 133, a back propagation unit 134, a cycle unit 135, a pruning unit 136, the graph output unit 137, and an erase unit 138. In some implementations, generation of a K-mer graph by the hardware-accelerated graph generation unit 130 can include the control machine 140 activating and configuring each of the hardware logic units 131 to 138 to execute their respective hardware logic operations on a set of data stored in the cache 150 or the DRAM 160. In other implementations, the control machine 140 may only activate and configure a subset of the hardware logic units 131 to 138 to execute their respective hardware logic operation on a set of raw graph data stored in the cache 150 or the DRAM 160.

By way of example, in some implementations, the hardware-accelerated graph generation unit 130 can be used to generate a specialized form of a De Bruijn graph. This specialized form of a De Bruijn graph can be optimized so that non-unique K-mers are represented using multiple respective nodes in a graph each with a single edge rather than being represented by a single node with multiple edges. This can be achieved, in part, by using a graph unit 132 to identify non-unique K-mers and flag the non-unique K-mers for further processing. A non-unique K-mer may be defined as a K-mer sequence which occurs at least twice in any single read, or at least twice in the reference sequence. A unique K-mer do not occur more than once in the same read, but may still occur in multiple reads.

However, in other implementations, De Bruijn graphs can be generated without distinguishing between unique or non-unique K-mers. Thus, in some implementations a graph node unit 132 that can identify non-unique K-mers need not be implemented. In yet another example, the back propagation unit 134 need not be used to generate all K-mer graphs. Instead, the back propagation unit 134 may be limited to implementations where it can improve performance. By way of example, the back propagation unit 134 can be used to improve the quality of edge weights when later transformation of a generated K-mer graph into a sequence graph is anticipated.

The K-mer graph generation example described with respect to the example of FIG. 1 shows each hardware logic unit 131 to 138 that can be activated and configured by the control machine 140. In this description, each hardware logic unit 131 to 138 is generally described as activated by the control machine 140, configured by the control machine 140 using, for example, graph description data stored by the control machine 140, obtaining raw graph data, performing one or more specific processing operations on the obtained raw graph data or other data, and then updating the raw graph data, the graph description data, or both, the present disclosure is not so limited. However, the present disclosure is not limited to such implementations. Instead, in some implementations, each hardware logic units 131 to 138 can be configured to execute multiple instances of its respective functionality. For example, graph node unit 132 can be configured to accept up to 3 distinct sets of raw graph data and simultaneously perform its operations thereon, the cycle hardware logic unit 135 can be configured to accept up to 3 distinct sets of raw graph data and simultaneously perform its operations thereon, and PRU can be configured to accept up to 2 distinct sets of raw graph data and simultaneously perform its operations thereon. The number of distinct sets or raw graph data that each correspond to different K-mer graphs can be received and processed by a particular hardware logic unit 131 to 138 is only limited by available hardware resources for a system 100. For example, assuming sufficient levels of DRAM and FPGA logic units are available for use, the number of distinct sets of raw graph data that can be received and simultaneously processed by a hardware logic unit 131 to 138 can be greater than 3. Likewise, one or more hardware logic units 131 to 138 can be configured to receive and simultaneously process lower numbers of sets of raw graph data if such resources are not readily available or if a particular hardware logic unit is not expected to be heavily used.

In yet other implementations, there is no requirement for there to be only one instance of each hardware logic unit 131 to 138 that are each capable of simultaneously processing distinct sets of raw graph data that each correspond to different K-mer graphs. Instead, in some implementations, multiple instances of each hardware-accelerated graph generation unit 130 can be configured to include multiple instances of one or more of the hardware logic units 131 to 138. In such instances, the control machine 140 can be configured to monitor the status and availability of each hardware logic unit 131 to 138, and then activate and configure each hardware logic unit in a manner that load balances processing operations across each respective hardware logic unit. For example, in some implementations, a hardware-accelerated graph generation unit 130 can be configured to have 3 instances of a graph node unit 132 that are each capable of receiving up to 3 distinct sets of raw graph data and simultaneously perform its operations on them, 3 instances of a graph edge unit 133 that are each capable of receiving up to 3 distinct sets of raw graph data and simultaneously performing its operations on them, 2 back propagation units 134 that are each capable of receiving up to 2 distinct sets of raw graph data and simultaneously performing its operations on them, and 3 cycle units 135 that are each capable of receiving up to 2 distinct sets of raw graph data and simultaneously perform its operations on them. Activation/deactivation of each hardware logic unit, configuration of each hardware logic unit, inputs to each hardware logic unit, outputs from each hardware logic unit, and updating of graph description data by each hardware logic unit is managed and directed by the control machine 140.

Input Unit

The input unit 131 can receive input data that includes the generated pileup of reads 112 and the selected reference genome 122, which can be referred to herein as being raw graph data. The selected reference genome 122 can include a portion of a reference genome. Raw graph data can include, for example, data that is processed by one or more hardware logic units 131 to 138 during generation of an instance of a K-mer graph. While raw graph data includes, for example, the generated reads 112 and the selected reference genome 122, raw graph data can also include, for example, K-mer nodes generated by the graph node unit

132, edges generated by the graph edge unit 133, and the like. The input unit 131 can format the generated reads 112 and the obtained reference genome 122 for storage in the DRAM 160. Formatting the generated reads can include, for example, encoding the reads for storage in the DRAM 160. In some implementations, encoding the read can include encoding each base call corresponding to a nucleotide of the read into 4-bit values. For example, an A can be encoded as 0000, a C can be encoded as 0001, a G can be encoded as 0010, a T can be encoded as 0011, and an N can be encoded as 0100, where N is an unknown base call. In some implementations, the encoded data can also include data that represents a MAPQ score, a read number, a sequence length, SAM flags, the base calls or nucleotides of the read, one or more quality indicators for the read other than the MAPQ score, or any combination thereof. The encoded read data can range from a 16-bit value to a 64-bit value, or more, that describes the read. The input unit 131 can write the generate reads to the DRAM 160.

The control machine 140 can detect receipt of the raw input data, activate the input unit 131, and initialize graph description data that corresponds to an instance of a K-mer graph that is to be generated based on the raw input data. Activating the input unit 131 can include the control machine 140 sending one or more control messages to the input unit 131 that instruct the input unit 131 to perform operations defined by the input unit's 131 hardware logic circuitry on the raw data provided as an input to the input unit 131. In some implementations, activating a hardware logic unit such as input unit 131 can also include the control machine providing, to the hardware logic unit, graph description data that can be used to configure the hardware logic unit for performance of its operations. Configuring the hardware logic unit can include, for example, providing pointers to cache storage locations storing K-mers, K-mer nodes, providing information describing K-mer length, or the like that the hardware logic unit needs to operate on.

Initializing the graph description data can include, for example, the control machine 140 generating a K-mer graph identifier for the raw input data, generation of a graph state information data structure, or a combination thereof. The K-mer graph identifier includes a data string of one or more characters, one or more numbers, or a combination thereof, that can be used to identify an instance of a K-mer graph throughout the K-mer graph generation process from the time that the raw graph data is received by the input unit 131 to at least the time that the erase unit 138 is used to remove data related to the K-mer graph identifier from the cache 150, DRAM 160, or both, following complete generation of the K-mer graph for a particular set of raw graph data. In some implementations, the K-mer graph identifier can include a number such as a 6-bit number having a value between 0-63. In some implementations, the K-mer graph identifier can even be used to refer to the K-mer graph after the erase unit is used to remove the aforementioned data from the cache 150, DRAM 160, or both. The graph state information data structure is a data structure having one or more fields that store data describing the current state of an instance of a K-mer graph that is to be generated for a particular set of raw input data. The state information can include, for example, data indicating a last hardware logic unit that operated on raw graph data for a particular instance of a K-mer graph, data indicating whether the last hardware logic unit aborted the operation, data indicating a K-mer length, data indicating a K-mer node list, data indicating a list of pointers that can be used to identify the K-mer nodes in a cache, a length of a K-mer node list, data indicating a list of non-unique K-mers, data indicating the locations of raw input data in the cache or DRAM, data indicating a base address in DRAM for nodes of the instance of a K-mer graph, or any subset or combination thereof.

The input unit 131 can format the input reads 112 and the reference genome 122 and write the input reads 112 and the reference genome to the DRAM 160. The control machine 140 can detect when the input unit 131 has completed formatting and writing of the input reads 112 and the reference genome 122 to the DRAM 160. Upon detection, by the control machine 140, of the completion of the formatting and writing of the input reads 112 and the reference genome 122 to the DRAM, the control machine 140 can update the graph state information to indicate that the input unit 131 has completed its operations on first raw graph data for a first instance of a K-mer graph.

Once the first raw graph data has been input, formatted, and stored in the DRAM 160, the control machine 140 can determine a next hardware logic unit that is to be activated and configured next. For example, the control machine 140 can activate and configure a graph node unit 132 to generate K-mer nodes based on the portion of the reference genome 122 and pileup of reads formatted and stored in the DRAM 160.

Graph Node Unit

The control machine 140 can activate and configure the graph node unit 132 to continue generation of the first instance of a K-mer graph by processing the formatted reads 112 and the reference genome 122 stored in the DRAM. This can include, for example, sending a control signal to the graph node unit 132, providing graph description data to the graph node unit 132, or a combination thereof. The graph description data can be used to configure the graph node unit 132 for operation. For example, providing the graph description data to the graph node unit 132 and from the control machine 140 can configure the graph node unit 132 to identify K-mers of particular size that is defined by the graph description data. Other fields of the graph description data described herein can be used to configure a hardware logic unit such as the graph node unit 132 in a similar manner.

In addition, in a substantially parallel manner, the control machine 140 can detect that the input unit 131 received second raw graph data as an input. The control machine 140 can then activate the input unit 131, instruct the unit 131 to format the reads and reference genome of the second raw graph data, and generate second graph description data for a second instance of a K-mer graph that is to be generated based on the second raw graph data. Thus, the control machine 140 can achieve high levels of throughput by simultaneously managing performance of different hardware logic units 131, 132 that are performing K-mer graph generation processes on different sets of raw graph data at different processing stages. The control machine 140 is configured to manage this parallel functionality across each of the hardware logic unit 131, 132, 133, 134, 135, 136, 137, 138 such at any particular point in time there may be as many as eight hardware logic units operating on eight different sets of raw graph data, with the hardware-accelerated graph generation unit 130 working towards generating eight different K-mer graphs simultaneously. The control machine 140, using the graph description data, manages this process throughout by activating and configuring each respect hardware logic unit to achieve abstractly high-level pipelined functionality out of the non-pipelined hardware logic units 131, 132, 133, 134, 135, 136, 137, 138, which do not have a direct and physical input/output connection between each respective hardware logic unit. Though an example of eight simultaneous K-mer graph generations being performed at the same time is illustrated, the present disclosure can be configured to achieve many more simultaneous K-mer graph generations such as by implementing multiple hardware-accelerated graph generation units 130 at a time, multiple instances of multiple hardware logic units on one or more hardware-accelerated graph generation units 130, or a combination thereof.

The graph node unit 132 can analyze each read of a pileup of reads 112 to identify each of the K-mers of the read. This can include, for example, sliding a K-mer access window along each position of each read to identify each particular K-mer of the respective read. The graph node unit 132 can store data representing a node of a K-mer graph, for each identified K-mer of each read, in the cache 150. Likewise, the graph node unit 132 can also generate and store, in DRAM, a list of node pointers in a data structure of node pointers, with each node pointer pointing to a K-mer node cache location. The graph node unit 132 can also generate and store information indicating the location and length of the list of node pointers for each K-mer graph in graph description data maintained by the control machine. These pointers can be used as graph state information, by the control machine 140, to configure another hardware logic unit during a subsequent portion of the K-mer graph generation process. The cache 150 can employ one or more cache coherency policies such as an LRU cache coherency policy that is configured to evict the oldest objects of the cache 150, with the oldest objects being determined based on the time the object was written to the cache 150.

Figure 4:
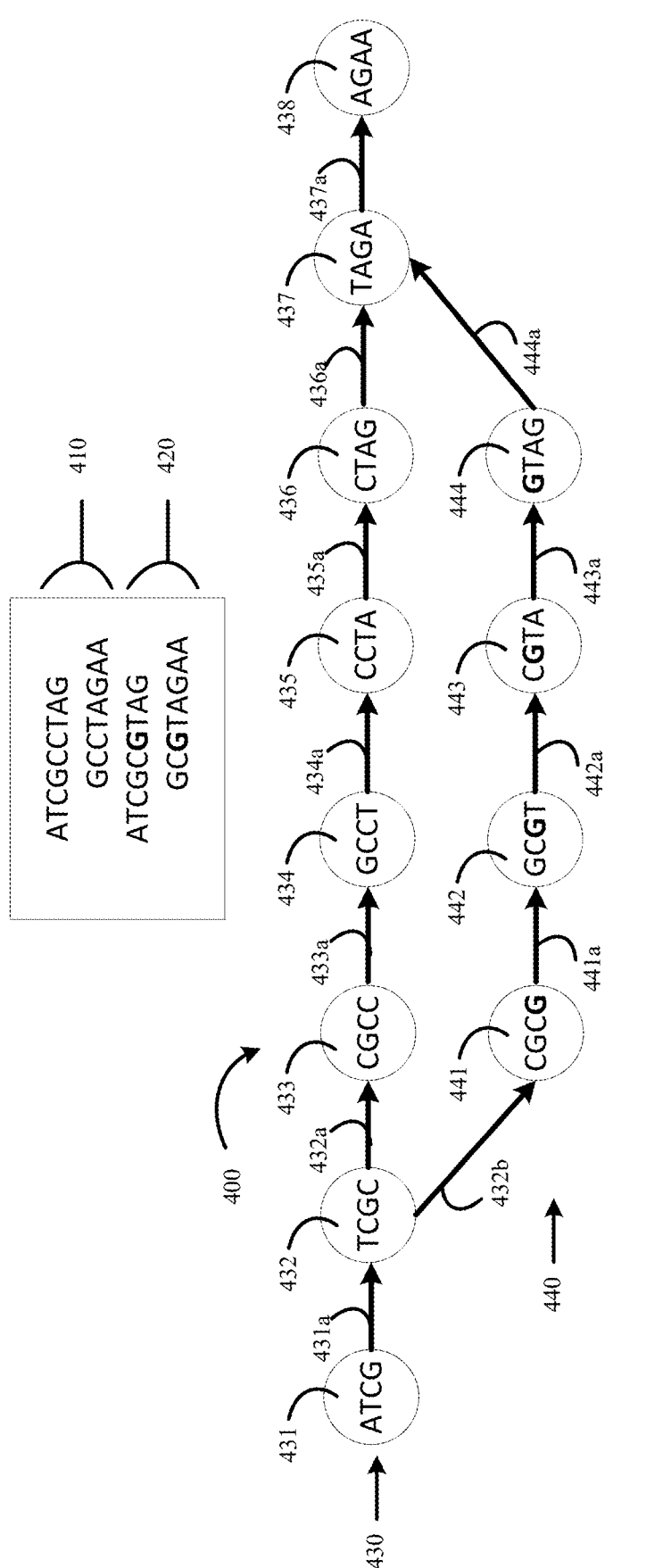
FIG. 4 is an example of a K-mer graph.

An example of data generated by the graph node unit 132 and stored in the cache 150, the DRAM 160, or both is shown with reference to FIG. 4. FIG. 4 shows a portion of a reference genome 410, a read 420, and a De Bruijn graph 400 is provided. The De Bruijn graph 400, which is described in more detail below, includes a node for each K-mer in the portion of the genome 410 and the read 420 and an edge between each pair of K-mer nodes that links a pair of nodes having k−1 overlapping nucleotides.

With reference to the example of FIG. 4, the graph node unit 132 can generate, based on receipt of a portion of the reference genome 410 and the read 420, data representing the nodes 431, 432, 433, 434, 435, 436, 437, 438 of a first path 430 of the De Bruijn graph 400 and nodes 441, 442, 443, 444 can be generated. First, the graph node unit 132 can align the overlapping portions of the reference genome 410a, 410b and the overlapping portions of the read 420a, 420b to identify overlapping regions as shown in FIG. 4. The graph node unit 132 can identify each of the K-mers of the portion of the genome 410 and the read 420. This can be achieved by using an access window of length k, which equals 4 in this example, at a first position of the portion of the reference genome 410 capturing the K-mer identified by the access window, generating data representing a node of the graph that includes the captured K-mer, storing the data representing the node in cache 150, advancing the access window by one nucleotide, and then iteratively repeating this process. In this example, the graph node unit 132 can identify the K-mers ATCG, TCGC, CGCC, GCCT, CCTA, CTAG, TAGA, and AGAA for the portion of the reference genome 410 and generate a respective node 431, 432, 433, 434, 435, 436, 437, 438, with one of these nodes corresponding to a respective K-mer. Each node is created to have a length of k, which is 4 in this example, and have an overlapping number of k−1 K-mers with the next adjacent node. The graph node unit 132 can store the generated nodes in the cache 150, the DRAM 160, or both. In some implementations, cache can include a hash table cache. In such implementations, the nodes can be stored as keys of a hash table. The graph node unit 132 can store data describing pointers to K-mer node locations in the graph description data maintained by the control machine 140.

The graph node unit 132 can perform the same operations for the read 420. With respect to the read 420, the graph node unit 132 can identify the K-mers ATCG, TCGC, CGCG, GCGT, CGTA, GTAG, TAGA, and AGAA. This can be similarly achieved by using an access window of length k, which is equal to 4 in this example, at a first position of the portion of the read 420 capturing the K-mer identified by the access window, and then advancing the access window and repeating the process. The graph node unit 132 can begin by identifying each K-mer for portion of the genome 410. In some implementations, the graph node unit 132 can generate a corresponding node for each of the K-mers. In other implementations, the graph node unit 132 may only generate 431, 432, 433, 434, 435, 436, 437, 438 corresponding to the identified K-mers that differ from the K-mer nodes of the portion of the reference genome 410. In each scenario, each node is created to have a length of k, which is 4 in this example, and have an overlapping number of k−1 K-mers with the next adjacent node. This can continue until a node for each K-mer of the portion of the reference genome 410 is created and stored in the cache 150 or DRAM 160.

In some implementations, the graph node unit 132 can also be configured to identify non-unique K-mers. In such implementations, the graph node unit 132 can for each particular read of a first pileup of reads, determine whether an identified K-mer is a unique K-mer or a non-unique K-mer. If the graph node unit 132 determines that a particular K-mer is a unique K-mer, then the graph node unit 132 can advance the access window by a single nucleotide to evaluate the next K-mer. Alternatively, if the graph node unit 132 determines that a particular K-mer is a non-unique K-mer, then the graph node unit 132 can store data indicating that the particular K-mer is a non-unique K-mer. For example, the graph node unit 132 can store a data flag in the graph description data maintained by the control machine for the particular instance of a K-mer graph indicating that the K-mer is a non-unique K-mer. However, such data can be stored by any other component of the hardware-accelerated graph generation unit 130, stored in any other memory unit of the hardware-accelerated graph generation unit 130, or a combination thereof. Then, subsequent hardware logic units can perform operations that address the non-unique K-mer in order to reduce or eliminate cycles in the instance of the K-mer graph.

At this point in the process, the graph node unit 132 stores the data representing a node of a K-mer graph for each K-mer in the cache 150, DRAM 160, or both. That is, the hardware-accelerated graph generation unit 130 has not yet generated the graph edges 431a, 432a 433a, 434a, 435a, 436a, 437a, 432b, 441a, 442a, 443a, 444a, graph edge weights, or the like. These features of this instance of a K-mer graph can be generated by one or more other hardware logic units of the hardware-accelerated graph generation unit 130.

The control machine 140 can monitor the operation of the graph node unit 132. Once the graph node unit 132 generates data representing a K-mer node for each K-mer of each read of the first raw graph data for this first instance of a K-mer graph, the control machine can update the graph description data to indicate that hardware-accelerated graph generation unit 130 has completed the graph node unit 132's operations on the first raw graph data. In addition, the control machine

140 can also store graph description data that includes, for example, a flag identifying each of the non-unique K-mers, storage locations for the K-mer graph nodes, and data indicating that the graph node unit 132 has completed its operations.

Once the K-mer graph nodes have been generated and stored in the cache 150, the control machine 140 can determine a next hardware logic unit that is to be activated and configured next. For example, the control machine 140 can activate and configure a graph edge unit 133 to generate, weight, or both, graph edges between pairs of nodes.

Graph Edge Unit

The graph edge unit 133 can generate graph edges between pairs of K-mer nodes generated by the graph node unit 132. The control machine 140 can activate the graph edge unit 133 once it is determined that the graph node unit 132 for the first K-mer graph instance is complete and that the graph edge unit 133 is available. In some implementations, the control machine 140 can provide, or otherwise make accessible to, the graph edge unit 133 locations storing K-mer graph nodes generated by the graph node unit 132 for a particular instance of a K-mer graph. For example, the control machine 140 can access K-mer graph description data generated and stored by the graph node unit 132 during generation of K-mer nodes for an instance of a K-mer graph. The accessed K-mer graph description data can indicate, or otherwise describe, a list of K-mers.

Once graph edge unit 133 has obtained the location of the K-mer graph nodes for the first instance of the K-mer graph, the graph edge unit can begin generating one or more graph edges between data representing the K-mer nodes. In some implementations, the graph edge unit 133 can access the data representing the graph node for each of the K-mers of the particular read from the hash table cache. The graph edge unit 133 can generate, for storage in the hash table cache, data representing a graph edge between the graph nodes for the K-mers. For example, the data representing the graph edge can be stored in the hash table cache as part of a graph node record for the edge's source node. In some implementations, the graph edge unit 133 can assign an edge weight to each edge of the K-mer graph. For example, the graph edge unit 133 can add a +1, or other weight, for each occurrence of the graph edge linking the respective K-mer pair.

By way of example, the graph edge unit 133 can identify nodes, using graph description data obtained from the control machine 140, that are adjacent nodes. The nodes can be determined to be adjacent nodes based on a variety of factors including a determination that the nodes share k−1 overlapping nucleotides and that the nodes are observed in two consecutive positions of the sliding K-mer access window. For example, graph edge unit 133 can slide a K-mer access window along each position of each read of the raw graph data. In some implementations, the graph edge unit 133 can create an edge or increment an edge weight upon a determination that two successive K-mers, which overlap by all but one base, are observed in a read. The graph node 133 creates an edge or increments an edge weight in such a scenario because this scenario implies an edge between the graph nodes corresponding to those two successive K-mers.

In some implementations, data representing the graph nodes can be stored as hash keys of a hash table. In such implementations, the graph edge unit 133 can generate an edge from a first node (or hash key) to a second node (or hash key) by accessing a hash location that the first node (or hash key) is mapped to and generating a pointer for stored in the hash location that points to the second node (or hash key). Subsequent edges can be generated in the same manner, which creates a path 430 or 440 through a graph that can be walked using one or more graph walking algorithms.

With reference to the example of FIG. 4, the graph edge unit 133 can generate data representing the one or more edges between pairs of nodes 431, 432, 433, 434, 435, 436, 437, 438 of a first path 430, pairs of nodes 441, 442, 443, 444 of a second path 440, or one or more pairs of nodes in the first path 430 and the second path 440. An example of these edges are shown in FIG. 4 as edges 431*a*, 432*a*, 433*a*, 434*a*, 435*a*, 436*a*, 437*a*, 432*b*, 441*a*, 442*a*, 443*a*, 444*a*.

In this example, the sequence of nucleotides 420 are referred to as a read. However, in some implementations, low quality base removal can occur such that the sequence of nucleotides 420 is a contig, or portion of a read. In such implementations, the graph edges linking a pair nodes will only create a path of one or more links within a particular contig and not from K-mer node of a first contig to a K-mer node of a second config. A contig can include a sequence of nucleotides occurring after a low quality base is removed.

Back Propagation Unit

The hardware-accelerated graph generation unit 130 can include a back-propagation unit 134. However, the control machine 140 may only activate and configure the back-propagation unit 134 in certain implementations. For example, the control machine 140 may activate the back-propagation unit 134 when it is determined, by the control machine 140, that the K-mer graph being generated by a current set of raw graph data will be later transformed into a sequence graph. When activated, the back-propagation module 134 can receive graph description data from the control machine 140. In such implementation, adjustments to graph edge weights can make the weights more reliable when inherited by the sequence graph.

The graph edge unit 133 can build edges between K-mer nodes of contigs by identifying corresponding K-mer nodes in the cash 150, generating an edge that links the K-mer nodes, and then incrementing a weight for the edge +1 for each occurrence. In some implementations, after the K-mer nodes of a contig have been added to a K-mer graph and weighted using the graph edge unit 134, the back-propagation unit 134 can be used to back propagate a +1 edge weight increments k–1 stages through a linear chain of graph edges "left" of the contig's starting node in the K-mer graph. In this context, "left" of the contig's starting node in the K-mer graph is a direction of a K-mer graph that is opposed the directed edge of the K-mer graph. To illustrate this concept, "left" of a node 434 in the De Bruijn graph 400 would be nodes 433, 432, and 431.

For example, in some implementations, the back propagation module 134 can access, in the hash table cache, the data representing the K-mer graph including its K-mer nodes, corresponding graph edges, or the like and then adjust edge weights for K–1 nodes that occur before a start of a new config. The back-propagation unit 135 can locate the appropriate K-mer nodes and edges to adjust based on graph description data received from the control machine 160 that includes pointers to cache locations storing this information. The graph description data can be updated with any changes that occur during back-propagation.

In some implementations, it can be advantageous to perform the aforementioned back-propagation because an N-base contig may only increment a series of (N-K) edge weights. However, if this K-mer graph is later transformed into a sequence graph with (N–1) internal edges corresponding to this contig, then the first (K–1) edge weights will not inherit properly incremented edge weights. The aforementioned back-propagation addresses most instances of this problem. Thus, back-propagation can be used to address this problem in order to increase the reliability of the inherited edge weights when the K-mer graph is transformed into a sequence graph.

Cycle Unit

The hardware-accelerated graph generation unit 130 can include a cycle unit 135. In some implementations, the cycle unit 135 can be activated and configured by the control machine 140 to detect cycles in an instance of a K-mer graph. For example, the cycle unit 135 can evaluate the K-mer nodes and K-mer edges of raw graph data of an instance of K-mer graph that has been generated by one or more of the input unit 131, graph node unit 132, graph edge unit 133, and back-propagation unit 134. The cycle unit 135 is configured to receive graph description data from the control machine 140. The cycle unit 135 can iteratively flag head nodes for deletion. A head node can include a node that does not include any in-edges. Where an in-edge is an edge that points to from a first node to the first node itself. After each head node is flagged for deletion, the cycle unit 135 can determine whether any nodes pointed to by out-edges have become head nodes as a results of a deleted node. If such nodes are determined, they are flagged for deletion. An out-edge is a graph edge that points from a first node to another node. The cycle unit 135 can continue performance of this process until there are no head nodes left.

Upon a determination that there are no head nodes left, the cycle unit 135 can determine whether the graph is empty, with an empty graph meaning that all nodes of the graph are flagged for deletion. If the headless graph is empty, then there was no cycle. Alternatively, if the headless graph is not empty, then the graph must contain a cycle. Cycles are resistant to this kind of deletion, because no node in a cycle becomes a head node by deleting nodes outside the cycle.

Upon making either one of these determinations, the cycle unit 135 can provide an indication to the control machine 140 as to whether or not a cycle was detected. Then, based on the provided indication from the cycle unit 135, the control machine 140 can determine which hardware logic unit should next be activated and configured. For example, if a cycle was detected and generation of the instance of the K-mer graph should be aborted, then the control machine 140 can activate and configure the erase unit 138. In such instances, the erase unit can delete raw graph data from the cache 150 and the DRAM 160 corresponding to the instance of the aborted K-mer graph. If, alternatively, generation of the instance of the K-mer graph is to continue, then control machine 140 can activate and configure another hardware logic unit to perform subsequent operations on the raw graph data to generate the instance of the K-mer graph. For example, if K-mer graph generation is to continue, the control machine 140 can either activate and configure the pruning unit 136 or the graph output unit 137.

Though the cycle unit 135 can be used by the hardware-accelerated graph generation unit 130 to detect cycles in an instance of a K-mer graph that is being generated, the cycle unit 135 can be selectively activated and configured like the back-propagation unit 134. This is because it is foreseeable some kinds of K-mer graphs can include cycles. However, for certain types of K-mer graphs, it may be beneficial to not have graphs with cycles. Accordingly, the hardware-accelerated graph generation unit 130 can be configured, for example, for the control machine 140 to receive input indicating whether or not the cycle unit 135 should be performed for a particular instance of a graph.

Pruning Unit

The hardware-accelerated graph generation unit 130 can include a pruning unit 135. Like the back-propagation unit 134 and the cycle unit 135, the pruning unit 136 can be selectively activated and configured by the control machine 160. If activated and configured, the pruning unit 135 can evaluate a weight of each graph edge in raw graph data for an instance of a K-mer graph that has been generated to this point by the hardware-accelerated graph generation unit 130. In some implementations, if the pruning unit 136 determines that the weight value of a graph edge fails to satisfy a predetermined threshold, then the pruning unit 136 can delete graph edge and any K-mer node that occurs after the identified graph edges. Alternatively, if the pruning unit 136 determines that the weight value of a graph edge satisfies the predetermined threshold, then the pruning unit 136 will leave the graph edge intact.

In other implementations, the pruning unit 136 can identify linear chains, where linear chains are maximal paths through the graph wherein all internal nodes between the start node and end node have exactly one in-edge and one out-edge. In such implementations, the pruning unit 136 can determine if every internal edge of the linear chain fails to satisfy the pruning threshold. If such a scenario occurs, the pruning unit 136 can delete the entire linear chain, including all internal edges and all internal nodes, except the chain's start node and/or end node, which the pruning unit 136 can retain if they have any non-interior edges.

Graph Output Unit

The hardware-accelerated graph generation unit 130 can include a graph output unit 137. The graph output unit 137 can be used, by the hardware-accelerated graph generation unit 130 to generate a final version 170 of the instance of the K-mer graph, as the instance of the K-mer graph is described by the graph description data and cached data. For example, the graph output unit 137 can obtain data representing the K-mer graph from the hash table cache 150 using the graph description data that includes, for example, pointers to locations in the hash table cache storing the K-mer graph data. Then, the graph output unit 137 can provide the data obtained from the hash table cache 150 describing the final version of the K-mer graph 170 to a variant calling unit 180. The variant calling unit 180 can perform variant calling analysis on the final version of the K-mer graph 170 to produce a set of variants 190. A set of variants 190 can include one or more candidate variants. A variant is an alteration in genomic data of an organism. A candidate variant is a determination by a variant calling unit that is inferred by the variant calling unit based on processing a K-mer graph 170. In some implementations, the candidate variant may have a threshold level of error in the variant determination.

The variant calling unit 180 can identify candidate variants by processing the K-mer graph 180. In some implementations, for example, the variant calling unit 180 can identify a candidate variant when a base call or nucleotide one or more reads in the pileup of reads and a nucleotide of a reference genome at a particular location of the reference genome are different. Data describing the set of variants 190 can be generated or determined in any number of ways. For example, in some implementations, variant calling operations can be performed as described in more detail in, for example, U.S. Pub. No. 2016/0180019, U.S. Pub. No. 2016/0306922, and U.S. Pub. No. 2019-0259468, the entire contents of each of which is hereby incorporated by reference in their entireties. Data describing the set of variants 190 can be provided for output in a number of different ways. For example, data describing the set of variants 190 can be displayed on a display of the nucleic acid sequencer 110, displayed on a display of a different computer, audibly output via one or more speakers of a computing device, output via a printer, or any combination thereof.

Erase Unit

The erase unit 138 can be used to perform memory reclamation tasks upon completion and output of an instance of a K-mer graph by the hardware-accelerated graph generation unit 130. For example, the erase unit can delete all raw graph data related to the particular instance of a K-mer graph that is completed and output by the hardware-accelerated graph generation unit 130. Alternatively, or in addition, the erase unit 138 can delete all data related to the particular instance of the graphical unit 130 that is stored by the control machine, delete all data related to the particular instance of the graphical unit 130 that is stored in DRAM 160, or the like. Accordingly, the erase unit 138 can selectively delete data representing graph nodes and data representing graph edges of the K-mer graph from the hash table cache. Such deletion is selective because only a portion of the contents of the cache, control machine, or DRAM needs to be removed. Moreover, when the graph is stored as a hash table, the hash table may often be sparsely populated, and it is faster for the erase unit 138 to selectively erase only the occupied hash table entries than to clear the entire hash table, thus resulting in performance improvements.

However, in some implementations, non-hash-table data associated with a graph does not need to be erased item by item. In such implementations, the erase unit 138 can set list lengths to zero in the graph description data or allocated memory space can just be freed for reuse without erasing the content.

FIG. 2 is a flowchart of an example of a process 200 for hardware-accelerated generation of a K-mer graph. In general, the process 200 can include obtaining a first set of nucleic acid sequences, wherein the first set of nucleic acid sequences includes (i) a plurality of reads corresponding to an active region of a reference sequence and (ii) a portion of the reference sequence (210), generating a K-mer graph using the obtained first set of nucleic acid sequences and using a plurality of non-pipelined hardware logic units of a programmable logic device, wherein each hardware logic unit comprises a different hardware logic circuit configured to perform one or more operations, wherein each node of the K-mer graph represents a K-mer, each edge of the graph represents a link between a pair of K-mers, and each weight of each edge of the K-mer graph represents a number of occurrences of a K-mer sequence represented by a pair of K-mers (220), during generation of the K-mer graph: periodically updating, with a control machine, graph description data for the K-mer graph after performance of the one or more operations by each hardware logic unit that is used to generate at least a portion of the K-mer graph, wherein the graph description data represents (i) a K-mer graph identifier and (ii) K-mer graph state information, wherein the control machine creates a workflow of operations using the non-pipelined hardware logic units by triggering performance of the one or more operations of each respective hardware logic unit during generation of the K-mer graph (230), and providing the K-mer graph to a variant calling module, wherein the variant calling unit processes the K-mer graph to determine one or more candidate variants between one or more of the plurality of reads and the reference sequence.

FIG. 3 is a flowchart of another example of a process 300 for hardware-accelerated generation of a K-mer graph. In general, the process 300 can include obtaining a first set of nucleic acid sequences, wherein the first set of nucleic acid sequences include (i) a plurality of reads corresponding to an active region of a reference sequence and (ii) a portion of the reference sequence (310), for each particular nucleic acid sequence of the first set of nucleic acid sequences: generating, for storage in a hash table cache and by a first hardware logic unit, data representing a graph node for each K-mer of the particular nucleic acid sequence (320), detecting, by a control machine, that the first hardware logic unit has completed generation of a graph node for each K-mer of the particular nucleic acid sequence (330), configuring, by the control machine, a second hardware logic unit to perform graph edge generation for the generated graph nodes (340), and for one or more pairs of the generated graph nodes: generating, by the second hardware logic units and for storage in the graph hash table, data representing graph edges between one or more pairs of the generated graph nodes generated by the first hardware logic unit, wherein the data representing the graph node for each K-mer stored in the hash table cache and the data representing graph edges stored in the hash table cache represents a K-mer graph of the first set of nucleic acid sequences (350).

FIG. 4 is an example of a K-mer graph 400. In this example, the K-mer graph is 400 is generated based on at least a portion of a reference genome 410 and a read 420. In this example, the K-mer graph 400 is a De Bruijn graph.

The K-mer graph 400 is generated using a plurality of nodes and one or more edges between pairs of nodes. Each node represents a K-mer of length k, wherein in this example k=4. Each edge provides an indication that there is an overlap of k–1 nucleotides of the K-mers linked by the edge. In the K-mer graph 400, the path 430 includes a plurality of nodes and edges that represent each K-mer of the portion of the reference sequence 410. Then, the path 440 includes a plurality of nodes and edges representing portions of a read 420 that differ from the portion of the reference genome 410.

Figure 5:
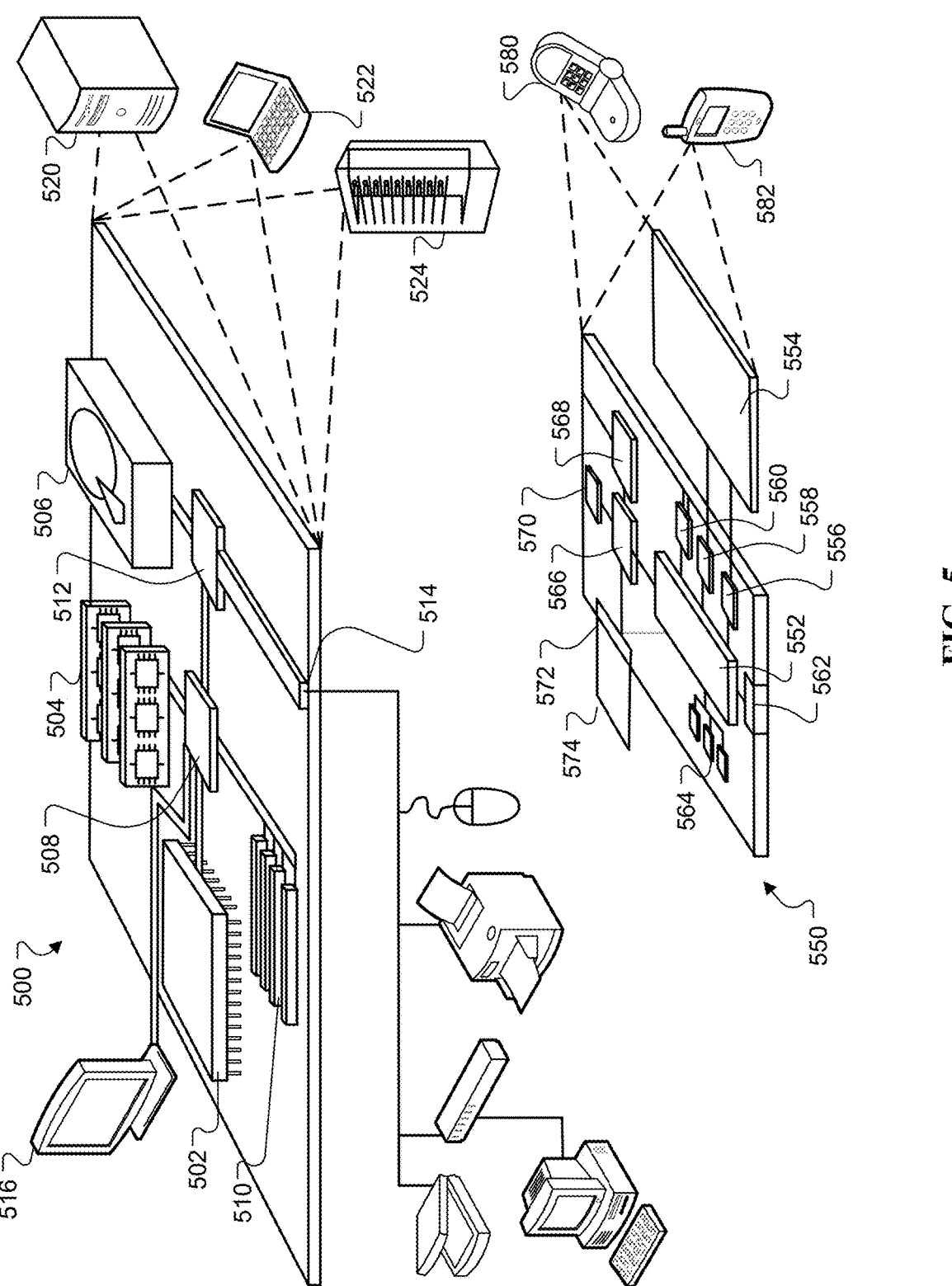
FIG. 5 is a block diagram of an example of system components that can be used for hardware-accelerated K-mer graph.

FIG. 5 is a block diagram of an example of system 500 components that can be used for hardware-accelerated K-mer graph.

Computing device 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smartphones, and other similar computing devices. Additionally, computing device 500 or 550 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be examples only, and are not meant to limit implementations of the inventions described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and can be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses can be used, as appropriate, along with multiple memories and types of memory. Also, multiple computing devices 500 can be connected, with each device providing portions of the necessary operations, e.g., as a server bank, a group of blade servers, or a multi-processor system.

The memory 504 stores information within the computing device 500. In one implementation, the memory 504 is a volatile memory unit or units. In another implementation, the memory 504 is a non-volatile memory unit or units. The memory 504 can also be another form of computer-readable medium, such as a magnetic or optical disk.

The storage device 506 is capable of providing mass storage for the computing device 500. In one implementation, the storage device 506 can be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 504, the storage device 506, or memory on processor 502.

The high-speed controller 508 manages bandwidth-intensive operations for the computing device 500, while the low speed controller 512 manages lower bandwidth intensive operations. Such allocation of functions is only an example. In one implementation, the high-speed controller 508 is coupled to memory 504, display 516, e.g., through a graphics processor or accelerator, and to high-speed expansion ports 510, which can accept various expansion cards (not shown). In the implementation, low-speed controller 512 is coupled to storage device 506 and low-speed expansion port 514. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.

The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.

Computing device 550 includes a processor 552, memory 564, and an input/output device such as a display 554, a communication interface 566, and a transceiver 568, among other components. The device 550 can also be provided with a storage device, such as a micro-drive or other device, to provide additional storage. Each of the components 550, 552, 564, 554, 566, and 568, are interconnected using various buses, and several of the components can be mounted on a common motherboard or in other manners as appropriate.

The processor 552 can execute instructions within the computing device 550, including instructions stored in the memory 564. The processor can be implemented as a chipset of chips that include separate and multiple analog and digital processors. Additionally, the processor can be implemented using any of a number of architectures. For example, the processor 510 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 550, such as control of user interfaces, applications run by device 550, and wireless communication by device 550.

Processor 552 can communicate with a user through control interface 558 and display interface 556 coupled to a display 554. The display 554 can be, for example, a TFT (Thin-Film-Transistor Liquid Crystal Display) display or an OLED (Organic Light Emitting Diode) display, or other appropriate display technology. The display interface 556 can comprise appropriate circuitry for driving the display 554 to present graphical and other information to a user. The control interface 558 can receive commands from a user and convert them for submission to the processor 552. In addition, an external interface 562 can be provided in communication with processor 552, so as to enable near area communication of device 550 with other devices. External interface 562 can provide, for example, for wired communication in some implementations, or for wireless communication in other implementations, and multiple interfaces can also be used.

The memory 564 stores information within the computing device 550. The memory 564 can be implemented as one or more of a computer-readable medium or media, a volatile memory unit or units, or a non-volatile memory unit or units. Expansion memory 574 can also be provided and connected to device 550 through expansion interface 572, which can include, for example, a SIMM (Single In Line Memory Module) card interface. Such expansion memory 574 can provide extra storage space for device 550, or can also store applications or other information for device 550. Specifically, expansion memory 574 can include instructions to carry out or supplement the processes described above, and can also include secure information. Thus, for example, expansion memory 574 can be provided as a security module for device 550, and can be programmed with instructions that permit secure use of device 550. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embod-ied in an information carrier. The computer program product contains instructions that, when executed, perform one or more methods, such as those described above. The information carrier is a computer- or machine-readable medium, such as the memory 564, expansion memory 574, or memory on processor 552 that can be received, for example, over transceiver 568 or external interface 562.

Device 550 can communicate wirelessly through communication interface 566, which can include digital signal processing circuitry where necessary. Communication interface 566 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 568. In addition, short-range communication can occur, such as using a Bluetooth, Wi-Fi, or other such transceiver (not shown). In addition, GPS (Global Positioning System) receiver module 570 can provide additional navigation- and location-related wireless data to device 550, which can be used as appropriate by applications running on device 550.

Device 550 can also communicate audibly using audio codec 560, which can receive spoken information from a user and convert it to usable digital information. Audio codec 560 can likewise generate audible sound for a user, such as through a speaker, e.g., in a handset of device 550. Such sound can include sound from voice telephone calls, can include recorded sound, e.g., voice messages, music files, etc. and can also include sound generated by applications operating on device 550.

The computing device 550 can be implemented in a number of different forms, as shown in the figure. For example, it can be implemented as a cellular telephone 580. It can also be implemented as part of a smartphone 582, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

OTHER EMBODIMENTS

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

The invention claimed is:

1. A method for hardware-accelerated generation of a K-mer graph using a programmable logic device, the method comprising:
   obtaining a first set of nucleic acid sequences, wherein the first set of nucleic acid sequences includes (i) a plurality of reads corresponding to a region of a reference sequence and (ii) a portion of the reference sequence;
   generating, using a plurality of non-pipelined hardware logic units of a programmable logic device a K-mer graph using the obtained first set of nucleic acid sequences, wherein each hardware logic unit comprises a different hardware logic circuit configured to perform one or more operations, wherein each node of the K-mer graph represents a K-mer, each edge of the K-mer graph represents a link between a pair of K-mers, and each weight of each edge of the K-mer graph represents a number of occurrences of a K-mer sequence represented by a pair of K-mers; and
   during generation of the K-mer graph:
      periodically updating, with a control machine, graph description data for the K-mer graph after performance of the one or more operations by each hardware logic unit that is used to generate at least a portion of the K-mer graph, wherein the graph description data represents (i) a K-mer graph identifier and (ii) K-mer graph state information, wherein the control machine creates a workflow of operations using the plurality of non-pipelined hardware logic units by triggering performance of the one or more operations of each respective hardware logic unit during generation of the K-mer graph.

2. The method of claim 1, wherein the output of each hardware logic unit of the plurality of non-pipelined hardware logic units is stored via a hash table cache.

3. The method of claim 1, wherein the control machine is implemented using a hardware logic unit of the programmable logic device.

4. The method of claim 1, wherein the control machine is implemented by using one or more CPUs or GPUs to execute software instructions to realize functionality of the control machine.

5. The method of claim 1, further comprising:
   providing the generated K-mer graph to a variant calling unit, wherein the variant calling unit processes the K-mer graph to determine candidate variants between one or more of the plurality of reads and the reference sequence.

6. The method of claim 5, wherein software instructions are executed by one or more CPUs or GPUs to realize one or more functions of the variant calling unit.

7. The method of claim 1, wherein the graph description data further includes (iii) data representing a last hardware logic unit of the plurality of non-pipelined hardware logic units that executed hardware logic on the K-mer graph or nucleic acid sequences of a pileup of reads associated with the K-mer graph identifier.

8. The method of claim 1, wherein during the generation of the K-mer graph further includes using the control machine to perform at least one of:
   activating one or more hardware logic units of the plurality of non-pipelined hardware logic units to perform the one or more operations defined for the one or more hardware logic units; and
   configuring at least one hardware logic unit of the plurality of non-pipelined hardware logic units to perform the one or more operations defined for the at least one hardware logic unit.

9. The method of claim 1, wherein based on updating the graph description data during the periodically updating, the control machine performs at least one of activating and configuring a selected hardware logic unit of the plurality of non-pipelined hardware logic units, wherein the selected hardware logic unit is to perform the one or more operations defined to be performed by the selected hardware logic unit.

10. A system for hardware-accelerated generation of a K-mer graph using a programmable logic device, the system comprising:
   a hardware-accelerated graph generation unit that includes hardware digital logic circuits that have been arranged to perform operations, the operations comprising:
      obtaining a first set of nucleic acid sequences, wherein the first set of nucleic acid sequences includes (i) a plurality of reads corresponding to a region of a reference sequence and (ii) a portion of the reference sequence;
      generating, using a plurality of non-pipelined hardware logic units of a programmable logic device a K-mer graph using the obtained first set of nucleic acid sequences, wherein each hardware logic unit comprises a different hardware logic circuit configured to perform one or more operations, wherein each node of the K-mer graph represents a K-mer, each edge of the K-mer graph represents a link between a pair of K-mers, and each weight of each edge of the K-mer graph represents a number of occurrences of a K-mer sequence represented by a pair of K-mers; and
during generation of the K-mer graph:
  periodically updating, with a control machine, graph description data for the K-mer graph after performance of the one or more operations by each hardware logic unit that is used to generate at least a portion of the K-mer graph, wherein the graph description data represents (i) a K-mer graph identifier and (ii) K-mer graph state information, wherein the control machine creates a workflow of operations using the plurality of non-pipelined hardware logic units by triggering performance of the one or more operations of each respective hardware logic unit during generation of the K-mer graph.

11. The system of claim 10, wherein the output of each hardware logic unit of the plurality of non-pipelined hardware logic units is stored via a hash table cache.

12. The system of claim 10, the system further comprising:
  one or more computers; and
  one or more memory devices storing instructions that, when executed by the one or more computers, cause the one or more computers to perform second operations of a variant calling unit, the second operations comprising:
    obtaining, by the variant calling unit, the generated K-mer graph; and
    identifying, based on the variant calling unit processing the generated K-mer graph, one or more candidate variants, wherein a candidate variant is a difference between a base call of one or more reads in a pileup of reads and a nucleotide of a reference genome at a particular location of the reference genome.

13. The system of claim 10, wherein the operations further include:
  obtaining, by a variant calling unit, the generated K-mer graph; and
  identifying, based on the variant calling unit processing the generated K-mer graph, one or more candidate variants, wherein a candidate variant is a difference between a base call of one or more reads in a pileup of reads and a nucleotide of a reference genome at a particular location of the reference genome.

14. The system of claim 10, wherein the graph description data further includes (iii) data representing a last hardware logic unit of the plurality of non-pipelined hardware logic units that executed hardware logic on the K-mer graph or nucleic acid sequences of a pileup of reads associated with the K-mer graph identifier.

15. The system of claim 10, wherein during the generation of the K-mer graph further includes using the control machine to perform at least one of:
  activating one or more hardware logic units of the plurality of non-pipelined hardware logic units to perform the one or more operations defined for the one or more hardware logic units; and
  configuring at least one hardware logic unit of the plurality of non-pipelined hardware logic units to perform the one or more operations defined for the at least one hardware logic unit.

16. A hardware-accelerated graph generation unit that includes hardware digital logic circuits that have been arranged to perform operations, the operations comprising:
  obtaining a first set of nucleic acid sequences, wherein the first set of nucleic acid sequences includes (i) a plurality of reads corresponding to a region of a reference sequence and (ii) a portion of the reference sequence;
  generating, using a plurality of non-pipelined hardware logic units of a programmable logic device a K-mer graph using the obtained first set of nucleic acid sequences, wherein each hardware logic unit comprises a different hardware logic circuit configured to perform one or more operations, wherein each node of the K-mer graph represents a K-mer, each edge of the K-mer graph represents a link between a pair of K-mers, and each weight of each edge of the K-mer graph represents a number of occurrences of a K-mer sequence represented by a pair of K-mers; and
  during generation of the K-mer graph:
    periodically updating, with a control machine, graph description data for the K-mer graph after performance of the one or more operations by each hardware logic unit that is used to generate at least a portion of the K-mer graph, wherein the graph description data represents (i) a K-mer graph identifier and (ii) K-mer graph state information, wherein the control machine creates a workflow of operations using the plurality of non-pipelined hardware logic units by triggering performance of the one or more operations of each respective hardware logic unit during generation of the K-mer graph.

17. The hardware-accelerated graph generation unit of claim 16, wherein during the generation of the K-mer graph further includes using the control machine to perform at least one of:
  activating one or more hardware logic units of the plurality of non-pipelined hardware logic units to perform the one or more operations defined for the one or more hardware logic units; and
  configuring at least one hardware logic unit of the plurality of non-pipelined hardware logic units to perform the one or more operations defined for the at least one hardware logic unit.

18. A method for hardware-accelerated generation of a K-mer graph using a programmable logic device, the method comprising:
  obtaining a first set of nucleic acid sequences, wherein the first set of nucleic acid sequences includes (i) a plurality of reads corresponding to a region of a reference sequence and (ii) a portion of the reference sequence;
  generating, using a plurality of non-pipelined hardware logic units of a programmable logic device a K-mer graph using the obtained first set of nucleic acid sequences, wherein each hardware logic unit comprises a different hardware logic circuit configured to perform one or more operations, wherein each node of the K-mer graph represents a K-mer, each edge of the K-mer graph represents a link between a pair of K-mers, and each weight of each edge of the K-mer graph represents a number of occurrences of a K-mer sequence represented by a pair of K-mers; and
  during generation of the K-mer graph:
    performing at least one of activating and configuring, using a control machine, a hardware logic unit of the plurality of non-pipelined hardware logic units to be used to generate at least a portion of the K-mer graph, the hardware logic unit to perform the one or more operations defined to be performed by the hardware logic unit;

updating, using the control machine, graph description data for the K-mer graph based on performance of the one or more operations by the hardware logic unit, wherein the graph description data represents at least one of (i) a K-mer graph identifier and (ii) K-mer graph state information; and performing at least one of activating and configuring, using the control machine, another hardware logic unit of the plurality of non-pipelined hardware logic units, based on the updating the graph description data, wherein the control machine creates a workflow of operations using the plurality of non-pipelined hardware logic units by triggering performance of the one or more operations of each respective hardware logic unit during generation of the K-mer graph.

19. A system for hardware-accelerated generation of a K-mer graph using a programmable logic device, the system comprising:

a hardware-accelerated graph generation unit that includes hardware digital logic circuits that have been arranged to perform operations, the operations comprising:

obtaining a first set of nucleic acid sequences, wherein the first set of nucleic acid sequences includes (i) a plurality of reads corresponding to a region of a reference sequence and (ii) a portion of the reference sequence;

generating, using a plurality of non-pipelined hardware logic units of a programmable logic device a K-mer graph using the obtained first set of nucleic acid sequences, wherein each hardware logic unit comprises a different hardware logic circuit configured to perform one or more operations, wherein each node of the K-mer graph represents a K-mer, each edge of the K-mer graph represents a link between a pair of K-mers, and each weight of each edge of the K-mer graph represents a number of occurrences of a K-mer sequence represented by a pair of K-mers; and during generation of the K-mer graph:

performing at least one of activating and configuring, using a control machine, a hardware logic unit of the plurality of non-pipelined hardware logic units to be used to generate at least a portion of the K-mer graph, the hardware logic unit to perform the one or more operations defined to be performed by the hardware logic unit;

updating, using the control machine, graph description data for the K-mer graph based on performance of the one or more operations by the hardware logic unit, wherein the graph description data represents at least one of (i) a K-mer graph identifier and (ii) K-mer graph state information; and performing at least one of activating and configuring, using the control machine, another hardware logic unit of the plurality of non-pipelined hardware logic units, based on the updating the graph description data, wherein the control machine creates a workflow of operations using the plurality of non-pipelined hardware logic units by triggering performance of the one or more operations of each respective hardware logic unit during generation of the K-mer graph.

20. A hardware-accelerated graph generation unit that includes hardware digital logic circuits that have been arranged to perform operations, the operations comprising:

obtaining a first set of nucleic acid sequences, wherein the first set of nucleic acid sequences includes (i) a plurality of reads corresponding to a region of a reference sequence and (ii) a portion of the reference sequence;

generating, using a plurality of non-pipelined hardware logic units of a programmable logic device a K-mer graph using the obtained first set of nucleic acid sequences, wherein each hardware logic unit comprises a different hardware logic circuit configured to perform one or more operations, wherein each node of the K-mer graph represents a K-mer, each edge of the K-mer graph represents a link between a pair of K-mers, and each weight of each edge of the K-mer graph represents a number of occurrences of a K-mer sequence represented by a pair of K-mers; and during generation of the K-mer graph:

performing at least one of activating and configuring, using a control machine, a hardware logic unit of the plurality of non-pipelined hardware logic units to be used to generate at least a portion of the K-mer graph, the hardware logic unit to perform the one or more operations defined to be performed by the hardware logic unit;

updating, using the control machine, graph description data for the K-mer graph based on performance of the one or more operations by the hardware logic unit, wherein the graph description data represents at least one of (i) a K-mer graph identifier and (ii) K-mer graph state information; and performing at least one of activating and configuring, using the control machine, another hardware logic unit of the plurality of non-pipelined hardware logic units, based on the updating the graph description data, wherein the control machine creates a workflow of operations using the plurality of non-pipelined hardware logic units by triggering performance of the one or more operations of each respective hardware logic unit during generation of the K-mer graph.

* * * * *